United States Patent [19]

Kise et al.

[11] Patent Number: 4,927,835
[45] Date of Patent: May 22, 1990

[54] ACYLPHENOL DERIVATIVES, USEFUL AS ANTI-INFLAMMATORY AGENTS AND PAIN SUPPRESSANTS

[75] Inventors: Masahiro Kise, Kyoto; Yoshihiko Yoshimoto, Kusatsu; Hiroshi Fujisawa, Otsu; Yasuo Sasaki, Kameoka; Shoji Yasufuku, Kyoto, all of Japan

[73] Assignee: Nippon Shinyaku Co., Ltd., Japan

[21] Appl. No.: 317,601

[22] Filed: Mar. 1, 1989

[30] Foreign Application Priority Data

Mar. 4, 1988 [JP] Japan .................... 63-51977

[51] Int. Cl.⁵ .................... A61K 31/38; A61K 31/34; A61K 31/40; C07D 333/22
[52] U.S. Cl. .................... 514/448; 514/227.5; 514/237.5; 514/255; 514/330; 514/423; 514/461; 544/57; 544/59; 544/157; 544/162; 544/337; 544/391; 546/22; 546/225; 546/226; 548/413; 548/561; 549/6; 549/72; 549/218; 549/488
[58] Field of Search .................... 549/72, 6; 514/448

[56] References Cited
U.S. PATENT DOCUMENTS
4,644,009  2/1987  Huang et al. .................... 549/72

Primary Examiner—Mary C. Lee
Assistant Examiner—J. Richter
Attorney, Agent, or Firm—Jacobs & Jacobs

[57] ABSTRACT

Compounds of the formula (I):

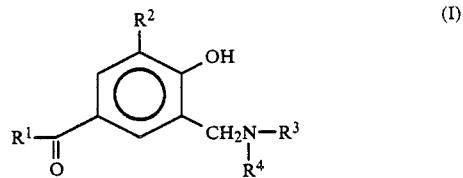

or a pharmaceutically acceptable salt thereof, wherein:
$R^1$ is cycloalkyl of 5 to 7 carbon atoms; aryl of 6 to 10 carbon atoms unsubstituted or substituted by straight or branched chain alkyl of 1 to 4 carbon atoms, halo or trifluoromethyl; or

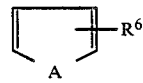

wherein A is oxygen, sulfur or $NR^5$, wherein $R^5$ is hydrogen, straight or branched chain alkyl of 1 to 4 carbon atoms or halo, and $R^6$ is hydrogen, straight or branched chain alkyl of 1 to 4 carbon atoms or halo;
$R^2$ is straight or branched chain alkyl of 1 to 4 carbon atoms or cycloalkyl of 5 to 7 carbon atoms; and
$R^3$ and $R^4$ are the same or different and each is hydrogen; straight or branched chain alkyl of 1 to 8 carbon atoms unsubstituted or substituted by hydroxy, acyloxy of 2 to 5 carbon atoms, carboxyl or carbamoyl;
are useful for treating pain, inflammation and fever in humans and animals.

24 Claims, No Drawings

ACYLPHENOL DERIVATIVES, USEFUL AS ANTI-INFLAMMATORY AGENTS AND PAIN SUPPRESSANTS

The present invention relates to acylphenol derivatives, pharmaceutical compositions containing said derivatives as the active agent, and to methods of producing analgesic, anti-inflammatory and anti-pyretic effects in humans and animals by administering said derivatives.

Various steroidal and nonsteroidal pharmaceuticals have been used as anti-inflammatory/analgesic agents. While steroidal compounds exhibit excellent anti-inflammatory action and show remarkable effects in the treatment of arthritis, rheumatism, etc., their continued use causes serious side effects such as hormonic imbalances which adversely affect the therapy. Nonsteroidal compounds also exhibit excellent anti-inflammatory action, but their continued use causes other undesirable side-effects, such as gastrointestinal disturbance.

It has been reported that some derivatives of 4-acyl-2,6-di-tert-butylphenol exhibit an inhibitory action to cyclooxygenase and inhibit carrageenin-induced edema. For instance, 3,5-di-tert-butyl-4-hydroxy-phenyl 2-thienyl ketone (known as R-830; cf. Agents and Actions, vol. 12, page 5, 1982) has been reported to exhibit inhibitory action against carrageenin-induced edema. The novel compounds of the present invention exhibit superior analgesic, anti-inflammatory, and anti-pyretic activity than R-830 and are also less toxic than R-830.

More particularly, the present invention relates to acylphenol derivatives of the formula (I)

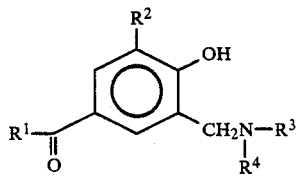

and pharmaceutically acceptable salts thereof, wherein:
$R^1$ is cycloalkyl of 5 to 7 carbon atoms; aryl of 6 to 10 carbon atoms unsubstituted or substituted by straight or branched chain alkyl of 1 to 4 carbon atoms, halo or trifluoromethyl; or

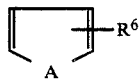

wherein A is oxygen, sulfur or $NR^5$, wherein $R^5$ is hydrogen, straight or branched chain alkyl of 1 to 4 carbon atoms or halo, and $R^6$ is hydrogen, straight or branched chain alkyl of 1 to 4 carbon atoms or halo;
$R^2$ is straight or branched chain alkyl of 1 to 4 carbon atoms or cycloalkyl of 5 to 7 carbon atoms; and
$R^3$ and $R^4$ are the same or different and each is hydrogen; straight or branched chain alkyl of 1 to 8 carbon atoms unsubstituted or substituted by hydroxy, acyloxy of 2 to 5 carbon atoms, carboxyl or carbamoyl; straight or branched chain alkenyl of 2 to 6 carbon atoms; straight or branched chain alkynyl of 2 to 6 carbon atoms; or cycloalkyl of 5 to 7 carbon atoms;
or $R^3$ and $R^4$, together with the nitrogen atom to which they are attached, form a cyclic amino moiety of 5 to 7 ring members wherein the nitrogen atom is the only heteroatom or which contains 1 or 2 additional heteroatoms selected from the group consisting of oxygen, sulphur and nitrogen, which cyclic amino moiety is unsubstituted or substituted by straight or branched chain alkyl of 1 to 4 carbon atoms, straight or branched chain hydroxyalkyl of 1 to 4 carbon atoms or hydroxy.

According to one embodiment of the present invention, $R^1$ is cycloalkyl of 5 to 7 carbon atoms. When $R^1$ is cycloalkyl, it is preferably cyclopentyl, cyclohexyl, or cycloheptyl.

According to another embodiment of the present invention, $R^1$ is aryl of 6 to 10 carbon atoms unsubstituted or substituted by straight or branched chain alkyl of 1 to 4 carbon atoms, halo, or trifluoromethyl. When $R^1$ is aryl, it is preferably phenyl, alpha-napthyl, or beta-naphthyl. When $R^1$ is substituted aryl, it is preferably substituted by methyl, ethyl, n-propyl, isopropyl, n-butyl, isobutyl, sec-butyl, tert-butyl, chloro, fluoro, bromo, iodo or trifluoromethyl.

In another embodiment of the present invention, $R^1$ is

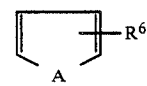

wherein A is oxygen, sulfur is $NR^5$, wherein $R^5$ is hydrogen, straight or branched chain alkyl of 1 to 4 carbon atoms or halo, and $R^6$ is hydrogen, straight or branched chain alkyl of 1 to 4 carbon atoms or halo. When $R^1$ is

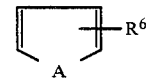

it is preferably 2-thienyl, 3-thienyl, 2-furyl, 3-furyl, 2-pyrrolyl, or 3-pyrrolyl. When $R^1$ is substituted

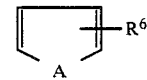

it is preferably substituted by methyl, ethyl, n-propyl, isopropyl, n-butyl, isobutyl, sec-butyl, tert-butyl, chloro, fluoro, bromo or iodo.

According to one embodiment of the present invention, $R^2$ is straight or branched chain alkyl of 1 to 4 carbon atoms, preferably methyl, ethyl, n-propyl, isopropyl, n-butyl, isobutyl, sec-butyl, or tert-butyl.

In another embodiment of the present invention, $R^2$ is cycloalkyl of 5 to 7 carbon atoms, preferably cyclopentyl, cyclohexyl, or cycloheptyl.

According to one embodiment of the present invention, $R^3$ and $R^4$ are hydrogen. In another embodiment of the present invention, $R^3$ and $R^4$ are the same or different and each is hydrogen; straight or branched chain alkyl of 1 to 8 carbon atoms unsubstituted or substituted by hydroxy, acyloxy of 2 to 5 carbon atoms, carboxyl or carbamoyl; straight or branched chain alkenyl of 2 to 6 carbon atoms; straight or branched chain alkynyl of 2 to 6 carbon atoms; or cycloalkyl of 5 to 7 carbon atoms. Preferred alkyl include methyl, ethyl, n-propyl, isopropyl, n-butyl, isobutyl, sec-butyl, tert-butyl, n-pentyl, isopentyl, n-hexyl, isohexyl, n-heptyl, isoheptyl, n-octyl and isooctyl. Preferred acyloxy substituents for alkyl include acetyloxy, propionyloxy and butyryloxy. Preferred alkenyl include vinyl, allyl, isopropenyl, 1,2-methallyl, 2-butenyl and 3-butenyl. Preferred alkynyl include ethynyl, 1-propynyl, or 2-propynyl. Preferred cycloalkyl are cyclopentyl, cyclohexyl and cycloheptyl.

In another embodiment of the present invention, $R^3$ and $R^4$, together with the nitrogen atom to which they are attached, form a cyclic amino moiety of 5 to 7 ring members wherein the nitrogen atom is the only heteroatom or which contains 1 or 2 additional heteroatoms selected from the group consisting of oxygen, sulfur and nitrogen, which cyclic amino moiety is unsubstituted or substituted by straight or branched chain alkyl of 1 to 4 carbon atoms, hydroxyalkyl of 1 to 4 carbon atoms or hydroxy. Preferred cyclic amino groups are pyrrolidino, piperidino, piperazino, morpholino, thiomorpholino, and homopiperazino. Preferred substituents for substituted cyclic amino moieties include methyl, ethyl, n-propyl, isopropyl, n-butyl, isobutyl, sec-butyl, tert-butyl, hydroxymethyl, hydroxyethyl, hydroxypropyl and hydroxybutyl.

Compounds of the present invention may be prepared as pharmaeutically acceptable salts with mineral acids, such as hydrochloric acid, sulfuric acid, nitric acid or phosphoric acid. Pharmaceutically acceptable salts may also be prepared with organic acids, such as oxalic acid, tartaric acid, maleic acid or benzenesulfonic acid.

The compounds of the present invention may, for example, be manufactured by the following reaction:

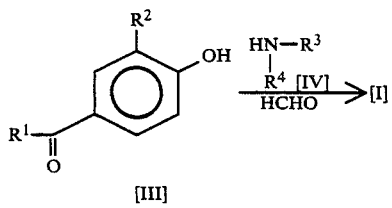

wherein $R^1$, $R^2$, $R^3$ and $R^4$ are as defined above with respect to formula (I).

Thus, compounds of the formula (I) of the present invention may be synthesized by reacting a p-acylphenol derivative (III) with a secondary amine (IV). This reaction is a so-called Mannich reaction. The reaction is carried out in the presence of an aldehyde either in the absence of solvent or in the presence of a solvent which is inert to the reaction. Suitable solvents which are commonly used in the reaction of this type include, for example, alcohols (e.g. methanol, ethanol, propanol, butanol, etc.), ethers (e.g. tetrahydrofuran, dioxane, etc.), aprotic solvents (e.g. acetonitrile, N,N-dimethylformamide, dimethyl sulfoxide, sulfolane, etc.), water, or mixtures thereof. Suitable aldehydes are those exhibiting the role of formaldehyde in a Mannich reaction. Such aldehydes include, for example, paraformaldehyde, formalin, methylal, ethylal, piperidinomethylphthalimide, hexamethylenetetramine, etc.

It is preferred that 1 to 10 molar equivalents of aldehyde and secondary amine be reacted per mole of p-acylphenol compound (III). The secondary amine may be used in a form of a salt. The reaction may be carried out at temperatures from about 0° to about 100° C. The reaction time may vary, depending upon the type of the starting materials and aldehyde used, the reaction temperature, etc. In most cases, however, the reaction can be completed in 1 to 40 hours.

The p-acylphenol starting materials (III) may themselves be novel compounds which may, for example, be manufactured via the following two reactions, which are further illustrated in the Referential Examples hereinafter:

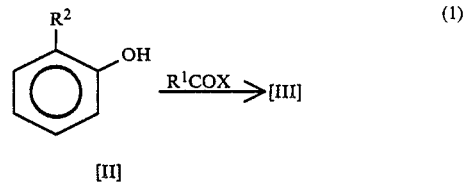

wherein $R^1$ and $R^2$ are the same as hereinbefore defined in formula (I) and wherein X is halo.

According to reaction (1), a phenol derivative (II) is reacted with an acid halide to give compound (III). This reaction is a Friedel-Crafts reaction or a similar reaction that and can be carried out in a solvent inert to the reaction in the presence of a Lewis acid if required.

The reaction may be carried out in solvents commonly used in reactions of this type. For example, carbon disulfide, nitrobenzene, halogenated hydrocarbons (e.g. chlorobenzene, dichloromethane, dichloroethane, trichloroethane, tetrachloroethane, etc.), aromatic hydrocarbons (e.g. benzene, toluene xylene, etc.), and the like may be used.

Examples of suitable Lewis acids include tin chloride, titanium chloride, zinc chloride, iron chloride, boron tribromide, boron trifluoride, concentrated sulfuric acid, etc. The use of titanium tetrachloride and stannic chloride is particularly preferred.

One to six molar equivalents of the Lewis acid chloride are reacted per mole of compound (II), preferably from an equimolar amount to a slight excess. The preferred reaction temperature is from about $-20°$ to about $+140°$ C. The reaction time may vary depending upon the materials, catalyst, reaction temperature, etc. but, usually, 4 to 12 hours are sufficient.

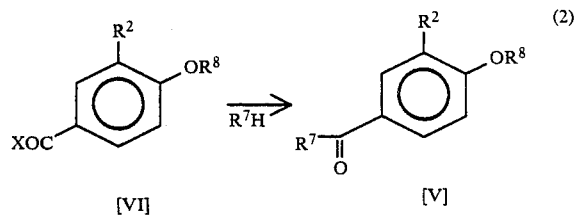

wherein $R^2$ is the same as hereinbefore defined in formula (I); X is halo; $R^8$ is a protective group for hydroxyl; and $R^7$ is aryl or an aromatic heterocycle represented by

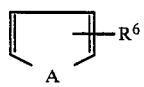

wherein A and $R^6$ are the same as hereinbefore defined in formula (I).

In synthesis (2), an acid halide (VI) is reacted with a compound of a formula $R^7H$ to provide compound (V). Removal of the protective group $R^8$ from compound (V) yields compound (III). Reaction (2) may be carried out under conditions substantially the same as in the above reaction (1).

Preferred protective groups represented by $R^8$ are those which are known as protective groups for hydroxyl such as, for example, lower alkyl, aralkyl and acyl.

In removing the protective group, conventional means, depending upon the particular protective group, may be used. For example, when $R^8$ is alkyl, dealkylation using acid may be used. When $R^8$ is aralkyl, reductive dearalkylation or hydrolysis using acid may be used. When $R^8$ is acyl, hydrolysis using an alkali may be used.

Synthesized compound (I) may be isolated and purified either as a free base or as an acid-addition salt by means of concentration, changing the pH of the liquid, dissolution in another solvent, extraction with a solvent, crystallization, recrystallization, fractional distillation, chromatography, and the like.

The present invention includes pharmaceutical compositions containing 0.1 to 99.5%, more particularly, 0.5 to 90% of a compound of the formula I or a pharmaceutically acceptable salt thereof in combination with a pharmaceutically acceptable carrier. These compositions can be formulated by procedures known in the art.

Oral administration can be effected utilizing solid and liquid dosage unit forms such as powders, tablets, capsules granules and the like.

Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agents can also be present.

Capsules are made by preparing a powder mixture as described above and filling formed gelatine sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds and pharmaceutically acceptable acid addition salts of the present invention can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a give quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected by utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservations and emulsifiers can also be added.

Rectal administration can be effected utilizing suppositories in which the compound is admixed with low-melting water-soluble or insoluble solids such as polyethylene glycol, cocoa butter, higher ester as for example flavored aqueous solution, while elixirs are prepared through myristyl palmitate or mixtures thereof.

The preferred pharmaceutical compositions are therefore those in a form suitable for oral administration, such as tablets and liquids.

While the dosage to be administered is based on the usual conditions such as the physical condition of the patient, age, body weight, past medical history, route of administrations, severity of the condition and the like, it is generally preferred to orally administer to a human from about 0.1 to 1,000 mg/day, more preferably from about 30 mg to about 600 mg/day until amelioration of the condition occurs. The dose may be divided if desirable and given during the course of each day. In some instances, a sufficient therapeutic effect can be obtained at a lower dose while in others, a larger dose will be required.

The following non-limitative Reference Examples illustrate preparation of starting materials from which compounds of present invention may be synthesized.

Reference Example A. 3-(1,1-Dimethylethyl)-4-hydroxybenzophenone.

Titanium chloride (20.86 g) was dissolved in 80 ml of 1,2-dichloroethane and 14.7 g of benzoyl chloride was added thereto with ice-cooling and stirring. 15.0 g of 2-tert-butylphenol was then added at the same temperature, and the mixture was stirred for 5 hours at ambient temperature. The reaction solution was poured into ice water and extracted with ether. The extract was sequentially washed with water, with an aqueous solution (saturated) of sodium bicarbonate, and with water, then dried with magnesium sulfate. The ether was evaporated and the residue was crystallized in n-hexane, yielding the desired compound. The compound was collected by filtration and dried to give 11.2 g of crystals.

Reference Example B. 3-(1,1-Dimethylethyl)-4-hydroxyphenyl 2-thienyl ketone.

Titanium tetrachloride (865.5 g) was dissolved in 2.3 liters of 1,2-dichloroethane and 502.2 g of 2-thenoyl chloride was added thereto over 20 minutes with ice cooling. Then, 517.4 g of 2-tert-butylphenol was added over 30 minutes and the mixture was stirred for 1.5 hours at room temperature. The reaction solution was poured over 2 kg of ice and extracted with 6.0 liters of ether. The extract was washed with water, with an aqueous solution of sodium bicarbonate, and with a saturated aqueous solution of sodium chloride, dried, and concentrated in vacuo. The concentrate was crystallized overnight in n-hexane. The crystals were then filtered, and washed with n-hexane to give 576.2 g of the desired compound as pale yellow crystals. M.p. 180°–181° C. (benzene).

By analogous procedures to those of Examples A and B, the following compounds were also prepared.
3-(1,1-Dimethylethyl)-4-hydroxy-4'-methylbenzophenone, m.p. 209°–210° C. (ethyl acetate);
4'-Chloro-3-(1,1-dimethylethyl)-4-hydroxybenzophenone, m.p. 205°–206° C. (ethyl acetate);
3'-Chloro-3-(1,1-dimethylethyl)-4-hydroxybenzophenone, m.p. 173°–174° C. (ligroin/ethyl acetate);
3-(1-Methylpropyl)-4-hydroxybenzophenone, m.p. 95°–96°C. (ligroin/ethyl acetate);
3-(1,1-Dimethylethyl)-4'-fluoro-4-hydroxybenzophenone, m.p. 203°–204° C. (ethyl acetate);
1-Naphthyl 3-(1,1-dimethylethyl)-4-hydroxyphenyl ketone, m.p. 177°–178° C. (ethyl actate);
Cyclohexyl 3-(1,1-dimethylethyl)-4-hydroxyphenyl ketone, m.p. 142°–143° C. (ethyl acetate/n-hexane);
3-Cyclohexyl-4-hydroxybenzophenone, m.p. 199°–200° C. (ethyl acetate);
(3-(1,1-Dimethylethyl)-2'-fluoro-4-hydroxybenzophenone, m.p. 152°–153° C. (n-hexane/ethyl acetate);
2-Naphthyl 3-(1,1-dimethylethyl)-4-hydroxyphenyl ketone, m.p. 189°–190° C. (ethyl acetate);
3-(1,1-Dimethylethyl)-4-hydroxyphenyl 2-furyl ketone, m.p. 146°–148° C.;
3-Cyclohexyl-4-hydroxyphenyl 2-thienyl ketone, m.p. 203°–204° C. (ether/n-hexane);
3-(1-Methylethyl)-4-hydroxyphenyl 2-thienyl ketone, m.p. 132°–133° C. (n-hexane);
3-(1-Methylpropyl)-4-hydroxyphenyl 2-thienyl ketone, m.p. 90°–92° C. (n-hexane);
3-(1,1-Dimethylethyl)-4-hydroxy-2'-trifluoromethylbenzophenone, m.p. 160°–161° C. (n-hexane); and
3-(1,1-Dimethylethyl)-4-hydroxy-2',6'-dichlorobenzophenone, m.p. 229°–230° C. (n-hexane).

Reference Example C. 3-(1,1-Dimethylethyl)-4-hydroxyphenyl 5-bromo-2-thienyl ketone.

3-(1,1-Dimethylethyl)-4-acetoxybenzoyl chloride (5.4 g) and 4.5 g of 2-bromothiophene were dissolved in 60 ml of 1,2-dichloroethane and, with ice cooling and stirring, 5.8 g of stannic chloride was added thereto. The reaction solution was stirred overnight at room temperature, poured over ice water and extracted with ether. The extract was washed with water and then with a saturated aqueous solution of sodium chloride. The ether was evaporated, and the residue was heated to reflux for 3 hours with 100 ml of a 10% aqueous solution of sodium hydroxide and 50 ml of ethanol. After the reaction, concentrated hydrochloric acid was added to the reaction solution and the acidified solution was extracted with ether. The extract was then washed with a saturated aqueous solution of sodium chloride and dried with magnesium sulfate. The ether was evaporated and the residue was subjected to a silica gel column chromatography followed by elution with chloroform. The fraction containing the desired product was concentrated and the resulting oil was crystallized from chloroform/n-hexane to give 4 g of crystals, m.p. 197°–199° C.

The following compounds were also prepared in accordance with the above procedure.
3-(1,1-Dimethylethyl)-4-hydroxyphenyl 5-methyl-2-thienyl ketone, m.p. 198°–200° C. (chloroform/n-hexane);
3-(1,1-Dimethylethyl)-4-hydroxyphenyl 4-methyl-2-thienyl ketone, m.p. 165°–166° C. (n-hexane); and
3-(1,1-Dimethylethyl)-4-hydroxyphenyl 3-methyl-2-thienyl ketone, m.p. 153°–155° C. (ethanol/water).

Reference Example D. 3-(1,1-Dimethylethyl)-4-hydroxyphenyl 5-chloro-2-thienyl ketone.

3-(1,1-Dimethylethyl)-4-methoxybenzoyl chloride (6.3 g) was dissolved in 55 ml of 1,2-dichloroethane and, with ice cooling and stirring, 6.0 g of titanium tetrachloride and then 3.7 g of 2-chlorothiophene were added thereto. The mixture was stirred overnight at room temperature, then poured over ice water and extracted with ether. The extract was washed sequentially with water, with an aqueous solution of sodium hydroxide, and with a saturated aqueous solution of sodium chloride then dried with magnesium sulfate. The ether was evaporated and the resulting residue was heated with stirring for 2 hours at 220°–230° C. with 24 g of pyridine hydrochloride. After the reaction, diluted hydrochloric acid was added and the mixture was extracted with ether. The extract was washed with water, dried with magnesium sulfate, and the liquid evaporated. The resulting oil was crystallized from chloroform and n-hexane and further recrystallized from ethanol/water to give 5.1 g of desired product, m.p. 200°–201° C.

Following the procedure of Example D the compound 3-(1,1-dimethylethyl)-4-hydroxyphenyl 3-chloro-2-thienyl ketone, m.p. 158°–159° C. was also prepared.

Reference Example E. 3-(1,1-Dimethylethyl)-4-hydroxyphenyl 1-methyl-2-pyrrolyl ketone.

3-(1,1-Dimethylethyl)-4-acetoxybenzoyl chloride (5.1 g) and 4.9 g of 1-methylpyrrole were dissolved in 150 ml of xylene and the mixture was heated at 140° C. for one day with stirring. 1-Methylpyrrole (4.0 g) was added to the reaction solution and the mixture was heated for two days with stirring at the same temperature as above. Xylene was evaporated therefrom, the residue was subjected to a silica gel column chromatography, and eluted with chloroform to give the desired acetate as an oil.

To this oil was added 30 ml of ethanol and 15 ml of 10% aqueous solution of sodium hydroxide. The mixture was then heated with refluxing for 1 hour, acidified with hydrochloric acid, and extracted with ether. The extract was washed with a saturated aqueous solution of sodium bicarbonate, dried with magnesium sulfate, and the ether was evaporated therefrom. The resulting oil was crystallized from chloroform and n-hexane, yielding 3.2 g of the desired product, m.p. 182°–183° C.

The following nonlimitative examples more particularly illustrate the present invention:

EXAMPLE 1

3-(N,N-Dimethylaminomethyl)-5-(1,1-dimethylethyl)-4-hydroxybenzophenone.

3-(1,1-Dimethylethyl)-4-hydroxybenzophenone (2.5 g), 1.71 g of dimethylamine hydrochloride, 0.78 g of sodium hydroxide, and 0.68 g of paraformaldehyde were dissolved in 30 ml of ethanol and the mixture was heated to reflux for 16 hours. The ethanol was then evaporate. Water was added to the residue and the crystals which separated out were filtered and recrystallized from 90% ethanol to give 2.1 g of the desire product, m.p. 129° C.

Elem. Anal ($C_{20}H_{25}NO_2$): Calcd (%) C: 77.14 H: 8.09 N: 4.50. Found (%) C: 77.27 H: 8.44 N: 4.53.

EXAMPLE 2

3-(N,N-Diethylaminomethyl)-5-(1,1-dimethylethyl)-4-hydroxybenzophenone hydrochloride.

3-(1,1-Dimethylethyl)-4-hydroxybenzophenone (1.27 g), 0.65 g of diethylamine and 35% aqueous solution of formaldehyde were dissolved in 30 ml of ethanol and the solution was heated to reflux with stirring for 8 hours. Ethanol was evaporated therefrom, hydrochloric acid was added to the residue, and the mixture was washed with ether. The hydrochloric acid layer was then made alkaline with an aqueous solution of sodium bicarbonate, and the oil separated out therefrom was extracted with ether. The extract was washed with water, dried with magnesium sulfate, and the ether was evaporated therefrom to give 0.86 g of oil. This oil was dissolved in 20 ml of ether, and the solution was allowed to stand for 1 hour with ethereal hydrochloric acid. Crystals which separated out were filtered and recrystallized from ethanol to give 0.5 g of crystals of m.p. 143°–145° C.

Elem. Anal. ($C_{22}H_{29}NO_2HCl$): Calcd (%) C: 70.29 H: 8.04 N: 3.72. Found (%) C: 70.28 H: 8.05 N: 3.77.

EXAMPLE 3

3-(N,N-Dimethylaminoethyl)-5-(1,1-dimethylethyl)-4-hydroxy-4'-methylbenzophenone.

3-(1,1-Dimethylethyl)-4-hydroxy-4'-methylbenzophenone (2.68 g) was suspended in 45 ml of ethanol and heated with stirring to reflux for 8 hours with 1.80 g of a 50% aqueous solution of dimethylamine and 1.7 g of a 35% aqueous solution of formaldehyde. Insoluble material was filtered off, the filtrate evaporated to dryness in vacuo, and the residue crystallized from ethanol to give 2.36 g of white crystals, m.p. 123°–124.5° C.

Elem. Anal. ($C_{21}H_{27}NO_2$): Calcd (%) C: 77.50 H: 8.36 N: 4.30. Found (%) C: 77.40 H: 8.68 N: 4.18.

EXAMPLE 4

3-(1,1-Dimethylethyl)-4-hydroxy-5-[N-(2-hydroxyethyl)-N-methylaminomethyl]phenyl 2-thienyl ketone.

3-(1,1-Dimethylethyl)-4-hydroxyphenyl 2-thienyl ketone (22.0 g) was dissolved in 440 ml of ethanol and heated to reflux for 6 hours with 12.7 g of N-methylethanolamine, 14.5 g of a 35% aqueous solution of formaldehyde and 50.8 g of acetic acid. After the reaction, the solvent was evaporated. A saturated aqueous solution of sodium bicarbonate was added to the residue and the mixture was extracted with chloroform three times. The extract was dried with magnesium sulfate, the solvent evaporated, and the resulting yellow oil subjected to a column chromatography (500 g of silica gel being used; eluates were (1) ethylacetate/n-hexane in 3:1 proportions and (2) the same in 1:1 proportion). The isolated and purified product was recrystallized from methanol/water to give 23.33 g of pale yellow crystals, m.p. 98°–100° C. (methanol/water).

Elem. Anal. ($C_{19}H_{25}NO_3S$): Calcd (%) C: 65.68 H: 7.25 N: 4.03. Found (%) C: 65.64 H: 7.26 N: 4.00.

The following additional nonlimitative Examples, which were prepared as hereinbefore described, further illustrate the compounds of the present invention:

EXAMPLE 5

3-(1,1-Dimethylethyl)-4-hydroxy-5-morpholinomethylbenzophenone hydrochloride.

M.p. 237°–239° C. (ethanol).

Elem. Anal. ($C_{22}H_{27}NO_3.HCl$): Calcd (%) C: 67.66 H: 7.24 N: 3.59. Found (%) C: 67.70 H: 7.37 N: 3.58.

EXAMPLE 6

3-(1,1-Dimethylethyl)-4-hydroxy-5-(N-methylpiperazinomethyl)benzophenone dihydrochloride.

M.p. 228°–230° C. (ethanol).

Elem. Anal. ($C_{23}H_{30}N_2O_2.2HCl.\frac{1}{2}H_2O$): Calcd (%) C: 61.94 H: 7.86 N: 6.24. Found (%) C: 61.60 H: 7.42 N: 6.25.

EXAMPLE 7

3-(N,N-Diethylaminomethyl)-5-(1,1-dimethylethyl-4-hydroxy-4'-methylbenzophenone.

M.p. 97°–99° C. (ethanol).

Elem. Anal. ($C_{23}H_{31}NO_2$): Calcd (%) C: 78.15 H: 8.84 N: 3.96. Found (%) C: 78.21 H: 8.53 N: 4.14.

EXAMPLE 8

3-(1,1-Dimethylethyl)-4-hydroxy-5-morpholinomethyl-4'-methylbenzophenone.

M.p. 131°–133° C. (ethanol).

Elem. Anal. ($C_{23}H_{29}NO_3$): Calcd (%) C: 75.17 H: 7.95 N: 3.81. Found (%) C: 75.00 H: 8.19 N: 3.94.

EXAMPLE 9

4'-Chloro-3-(N,N-dimethylaminomethyl)-5-(1,1-dimethylethyl)-4-hydroxybenzophenone hydrochloride.

M.p. 226°–228° C. (decomposition) (ethanol).

Elem. Anal. ($C_{20}H_{24}ClNO_2.HCl$): Calcd (%) C: 62.83 H: 6.59 N: 3.66. Found (%) C: 62.77 H: 6.81 N: 3.76.

EXAMPLE 10

4'-Chloro-3-(N,N-diethylaminomethyl)-5-(1,1-dimethylethyl)-4-hydroxybenzophenone.

M.p. 95°–96.5° C. (ethanol).

Elem. Anal. ($C_{22}H_{28}ClNO_2$): Calcd (%) C: 70.67 H: 7.55 N: 3.75. Found (%) C: 70.63 H: 7.63 N: 3.87.

EXAMPLE 11

4'-Chloro-3-(1,1-dimethylethyl)-4-hydroxy-5-morpholinomethylbenzophenone.

M.p. 165°–166° C. (ethanol).
Elem. Anal. ($C_{22}H_{28}ClNO_3$): Calcd (%) C: 68.12 H: 6.76 N: 3.61. Found (%) C: 68.17 H: 6.94 N: 3.71.

EXAMPLE 12

4'-Chloro-3-(1,1-dimethylethyl)-4-hydroxy-5-(N-methylpiperazinomethyl)benzophenone.

M.p. 131°–132° C. (ethanol).
Elem. Anal. ($C_{23}H_{29}ClN_2O_2$): Calcd (%) C: 68.90 H: 7.29 N: 6.99. Found (%) C: 68.92 H: 7.43 N: 7.08.

EXAMPLE 13

3'-Chloro-3-(N,N-dimethylaminomethyl)-5-(1,1-dimethylethyl)-4-hydroxybenzophenone.

M.p. 143°–145° C. (ethanol).
Elem. Anal. ($C_{20}H_{24}ClNO_2$): Calcd (%) C: 69.45 H: 6.99 N: 4.05. Found (%) C: 69.44 H: 7.22 N: 4.14.

EXAMPLE 14

3-(N,N-Dimethylaminomethyl)-5-(1,1-dimethylethyl)-4-hydroxyphenyl 2-thienyl ketone.

M.p. 132°–134° C. (ethanol).
Elem. Anal. ($C_{18}H_{23}NO_2S$): Calcd (%) C: 68.11 H: 7.30 N: 4.41. Found (%) C: 68.04 H: 7.34 N: 4.41.

EXAMPLE 15

3-(N,N-Dimethylaminomethyl)-5-(1,1-dimethylethyl)-5-hydroxyphenyl 2-thienyl ketone hydrochloride.

M.p. 211°–212° C.
Elem. Anal. ($C_{18}H_{23}NO_2S \cdot HCl$): Calcd (%) C: 61.09 H: 6.84 N: 3.96. Found (%) C: 61.07 H: 6.89 N: 4.25.

EXAMPLE 16

3-(1,1-Dimethylethyl)-4-hydroxy-5-pyrrolidinomethylphenyl 2-thienyl ketone.

M.p. 95°–97° C. (ethanol/water).
Elem. Anal. ($C_{20}H_{25}NO_2S$): Calcd (%) C: 69.94 H: 7.34 N: 4.08. Found (%) C: 69.98 H: 7.52 N: 4.07.

EXAMPLE 17

3-(1,1-Dimethylethyl)-4-hydroxy-5-piperidinomethylphenyl 2-thienyl ketone.

M.p. 132°–133° C. (ethanol).
Elem. Anal. ($C_{21}H_{27}NO_2S$): Calcd (%) C: 70.55 H: 7.61 N: 3.92. Found (%) C: 70.48 H: 7.69 N: 3.88.

EXAMPLE 18

3-(1,1-Dimethylethyl)-4-hydroxy-5-morpholinomethylphenyl 2-thienyl ketone.

M.p. 147.5°–148.5° C. (ethanol/water).
Elem. Anal. ($C_{20}H_{25}NO_3S$): Calcd (%) C: 66.82 H: 7.01 N: 3.90. Found (%) C: 66.83 H: 6.94 N: 3.93.

EXAMPLE 19

3-(1,1-Dimethylethyl)-4-hydroxy-5-(4-methylpiperazinomethyl)phenyl 2-thienyl ketone.

M.p. 118°–119° C. (ethanol/water).
Elem. Anal. ($C_{21}H_{28}N_2O_2S$): Calcd (%) C: 67.71 H: 7.58 N: 7.52. Found (%) C: 67.78 H: 7.56 N: 7.54.

EXAMPLE 20

3-(N,N-Diethylaminomethyl)-5-(1,1-dimethylethyl)-4-hydroxyphenyl 2-thienyl ketone hydrochloride.

M.p. 144°–145° C.
Elem. Anal. ($C_{20}H_{27}NO_2S \cdot HCl$): Calcd (%) C: 62.89 H: 7.39 N: 3.67. Found (%) C: 62.76 H: 7.29 N: 3.64.

EXAMPLE 21

3-(1,1-Dimethylethyl)-4-hydroxy-5-thiomorpholinomethylphenyl 2-thienyl ketone.

M.p. 165°–166° C. (ethanol).
Elem. Anal. ($C_{20}H_{25}NO_2S_2$): Calcd (%) C: 63.93 H: 6.71 N: 3.73. Found (%) C: 64.17 H: 6.55 N: 3.69.

EXAMPLE 22

3-(N,N-Dimethylaminomethyl)-5-(1,1-dimethylethyl)-4-hydroxyphenyl 5-methyl-2-thienyl ketone.

M.p. 119°–120° C. (ethanol/water).
Elem. Anal. ($C_{19}H_{25}NO_2S$): Calcd (%) C: 68.85 H: 7.60 N: 4.23. Found (%) C: 68.84 H: 7.72 N: 4.21.

EXAMPLE 23

3-(N,N-Dimethylaminomethyl)-5-(1,1-dimethylethyl)-4-hydroxyphenyl 5-chloro-2-thienyl ketone.

M.p. 137°–138° C. (ethanol).
Elem. Anal. ($C_{18}H_{22}ClNO_2S$): Calcd (%) C: 61.44 H: 6.30 N: 3.98. Found (%) C: 61.42 H: 6.34 N: 3.22.

EXAMPLE 24

3-(N,N-Dimethylaminomethyl)-5-(1,1-dimethylethyl)-4-hydroxyphenyl 5-bromo-2-thienyl ketone.

M.p. 150°–152° C. (ethanol).
Elem. Anal. ($C_{18}H_{22}BrNO_2S$): Calcd (%) C: 54.55 H: 5.59 N: 3.53. Found (%) C: 54.93 H: 5.59 N: 3.55.

EXAMPLE 25

3-(1,1-Dimethylethyl)-4-hydroxy-5-bis(2-hydroxyethyl)aminomethylphenyl 2-thienyl ketone.

M.p. 108°–110° C. (ethanol/water).
Elem. Anal. ($C_{20}H_{27}NO_4S$): Calcd (%) C: 63.63 H: 7.21 N: 3.71. Found (%) C: 63.47 H: 7.74 N: 4.15.

EXAMPLE 26

3-(N,N-Dimethylaminomethyl)-5-(1,1-dimethylethyl)-4-hydroxyphenyl 1-methyl-2-pyrrolyl ketone.

M.p. 173.5°–174.5° C. (ethanol).
Elem. Anal. ($C_{19}H_{26}N_2O_2$): Calcd (%) C: 72.58 H: 8.33 N: 8.91. Found (%) C: 72.55 H: 8.39 N: 8.94.

EXAMPLE 27

3-(N,N-Diethylaminomethyl)-4-hydroxy-5-(1,1-dimethylethyl)phenyl 2-furyl ketone hydrochloride.

M.p. 133°–135° C. (isopropanyl/ether).
Elem. Anal. ($C_{20}H_{27}NO_3 \cdot HCl$): Calcd (%) C: 65.65 H: 7.71 N: 3.83. Found (%) C: 65.30 H: 8.03 N: 4.05.

EXAMPLE 28

3-(N,N-Diethylaminomethyl)-5-(1,1-dimethylethyl)-4-hydroxyphenyl 1-methyl-2-pyrrolyl ketone hydrochloride.

M.p. 170°–172° C. (isopropanyl/ether).

Elem. Anal. ($C_{21}H_{30}NO_2O_2 \cdot HCl$): Calcd (%) C: 66.56 H: 8.25 N: 7.39. Found (%) C: 66.55 H: 8.36 N: 7.49.

EXAMPLE 29

3-(N,N-Dimethylaminomethyl)-5-(1,1-dimethylethyl)-4-hydroxyphenyl 3-chloro-2-thienyl ketone.

M.p. 131°–132° C. (ethanol).

Elem. Anal. ($C_{18}H_{22}NO_2ClS$): Calcd (%) C: 61.44 H: 6.30 N: 3.98. Found (%) C: 61.38 H: 6.03 N: 4.08.

EXAMPLE 30

3-(N,N-Dimethylaminomethyl)-5-(1,1-dimethylethyl)-4-hydroxyphenyl 3-methyl-2-thienyl ketone.

M.p. 149°–150° C. (ethanol).

Elem. Anal. ($C_{19}H_{25}NO_2S$): Calcd (%) C: 68.85 H: 7.60 N: 4.23. Found (%) C: 68.86 H: 7.47 N: 4.41.

EXAMPLE 31

3-(N,N-Dimethylaminomethyl)-5-(1,1-dimethylethyl)-4-hydroxyphenyl cyclohexyl ketone.

M.p. 149°–150° C. (ethanol).

Elem. Anal. ($C_{20}H_{31}NO_2$): Calcd (%) C: 75.66 H: 9.84 N: 4.41. Found (%) C: 75.81 H: 9.84 N: 4.63.

EXAMPLE 32

3-(N,N-Dimethylaminomethyl)-5-(1,1-dimethylethyl)-4-hydroxyphenyl 2-naphthyl ketone.

M.p. 162.5°–163.5° C. (ethanol).

Elem. Anal. ($C_{24}H_{27}NO_2$): Calcd (%) C: 79.74 H: 7.53 N: 3.87. Found (%) C: 79.66 H: 7.23 N: 4.00.

EXAMPLE 33

3-(N,N-Dimethylaminomethyl)-5-(1,1-dimethylethyl)-4-hydroxyphenyl 4-methyl-2-thienyl ketone hydrochloride.

M.p. 187°–189° C. (isopropanol).

Elem. Anal. ($C_{19}H_{25}NO_2S \cdot HCl$): Calcd (%) C: 62.02 H: 7.12 N: 3.81. Found (%) C: 61.95 H: 7.37 N: 3.94.

EXAMPLE 34

3-(N,N-Diethylaminomethyl)-5-(1,1-dimethylethyl)-2'-fluoro-4-hydroxybenzophenone hydrochloride.

M.p. 162° C. (ethanol).

Elem. Anal. ($C_{22}H_{28}FNO_2 \cdot HCl$): Calcd (%) C: 67.08 H: 7.42 N: 3.56. Found (%) C: 67.34 H: 7.46 N: 3.62.

EXAMPLE 35

3-(N,N-Diethylaminomethyl)-5-(1,1-dimethylethyl)-4-hydroxyphenyl 2-naphthyl ketone hydrochloride.

M.p. 175°–176° C. (isopropanol/ether).

Elem. Anal. ($C_{26}H_{31}NO_2 \cdot HCl$): Calcd (%) C: 73.31 H: 7.57 N: 4.03. Found (%) C: 73.22 H: 7.70 N: 4.15.

EXAMPLE 36

3-(N,N-Dimethylaminomethyl)-5-(1,1-dimethylethyl)-4'-fluoro-4-hydroxybenzophenone.

M.p. 112°–113° C. (ethanol).

Elem. Anal. ($C_{20}H_{24}FNO_2$): Calcd (%) C: 72.92 H: 7.34 N: 4.25. Found (%) C: 72.93 H: 7.20 N: 4.42.

EXAMPLE 37

3-(N,N-Diethylaminomethyl)-5-(1,1-dimethylethyl)-4'-fluoro-4-hydroxybenzophenone hydrochloride.

M.p. 177°–178° C. (isopropanol).

Elem. Anal. ($C_{20}H_{28}FNO_2 \cdot HCl$): Calcd (%) C: 67.08 H: 7.42 N: 3.56. Found (%) C: 67.14 H: 7.46 N: 3.75.

EXAMPLE 38

3-(1,1-Dimethylethyl)-4-hydroxy-5-[N-(2-hydroxyethyl)-N-methylaminomethyl]-4'-fluorobenzophenone hydrochloride.

M.p. 133°–134° C. (isopropanol/ether).

Elem. Anal. ($C_{21}H_{26}FNO_3 \cdot HCl$): Calcd (%) C: 63.71 H: 6.87 N: 3.54. Found (%) C: 63.77 H: 6.94 N: 3.63.

EXAMPLE 39

3-(N,N-Dimethylaminomethyl)-5-(1,1-dimethylethyl)-4-hydroxyphenyl 1-naphthyl ketone hydrochloride.

M.p. 210°–211° C. (isopropanol).

Elem. Anal. ($C_{24}H_{27}NO_2 \cdot HCl$): Calcd (%) C: 72.44 H: 7.09 N: 3.52. Found (%) C: 72.57 H: 6.93 N: 3.55.

EXAMPLE 40

3-(N,N-Diethylaminomethyl)-5-(1,1-dimethylethyl)-4-hydroxyphenyl 1-naphthyl ketone hydrochloride.

M.p. 173°–174° C. (isopropanol/ether).

Elem. Anal. ($C_{26}H_{31}NO_2 \cdot HCl$): Calcd (%) C: 73.31 H: 7.57 N: 3.29. Found (%) C: 73.21 H: 7.39 N: 3.54.

EXAMPLE 41

3-(1,1-Dimethylethyl)-4-hydroxy-5-morpholinomethylphenyl 1-naphthyl ketone.

M.p. 145°–146° C. (ethanol).

Elem. Anal. ($C_{26}H_{29}NO_3$): Calcd (%) C: 77.39 H: 7.24 N: 3.47. Found (%) C: 77.05 H: 7.22 N: 3.66.

EXAMPLE 42

3-(1,1-Dimethylethyl)-4-hydroxy-5-piperidinomethylphenyl 1-naphthyl ketone hydrochloride.

M.p. 218°–219° C. (ethanol).

Elem. Anal. ($C_{27}H_{31}NO_2 \cdot HCl$): Calcd (%) C: 74.04 H: 7.38 N: 3.20. Found (%) C: 74.20 H: 7.18 N: 3.30.

EXAMPLE 43

3-(1,1-Dimethylethyl)-4-hydroxy-5-[N-(2-hydroxyethyl)piperazinomethyl] benzophenone dihydrochloride.

M.p. 181°–182° C. (isopropanol/ether).

Elem. Anal. ($C_{24}H_{32}N_2O_3 \cdot 2HCl \cdot \frac{1}{2}H_2O$): Calcd (%) C: 60.24 H: 7.37 N: 5.85. Found (%) C: 60.28 H: 7.49 N: 5.88.

EXAMPLE 44

3-(1,1-Dimethylethyl)-4-hydroxy-5-(4-hydroxypiperidinomethyl) benzophenone.

M.p. 156°–157° C. (ethanol).

Elem. Anal. ($C_{23}H_{28}NO_3$): Calcd (%) C: 75.38 H: 7.70 N: 3.82. Found (%) C: 75.04 H: 7.97 N: 4.05.

EXAMPLE 45

3-Cyclohexyl-5-(N,N-diethylaminomethyl)-4-hydroxybenzophenone.

M.p. 106°–107° C. (ethanol).

EXAMPLE 46

3-(N,N-Dimethylaminomethyl)-4-hydroxy-5-(1-methylethyl)phenyl 2-thienyl ketone hydrochloride.

M.p. 170°–171° C. (isopropanol).
Elem. Anal. ($C_{17}H_{21}NO_2S.HCl$): Calcd (%) C: 60.08 H: 6.52 N: 4.12. Found (%) C: 60.06 H: 6.24 N: 4.22.

EXAMPLE 47

3-(N,N-Diethylaminomethyl)-4-hydroxy-5-(1-methylethyl)phenyl 2-thienyl ketone hydrochloride.

M.p. 168.5°–169.5° C.
Elem. Anal. ($C_{19}H_{25}NO_2S.HCl$): Calcd (%) C: 62.02 H: 7.12 N: 3.81. Found (%) C: 62.02 H: 7.04 N: 3.99.

EXAMPLE 48

3-Cyclohexyl-5-(N,N-dimethylaminomethyl)-4-hydroxyphenyl 2-thienyl ketone.

M.p. 105°–106° C. (ethanol/water).
Elem. Anal. ($C_{20}H_{25}NO_2S$): Calcd (%) C: 69.94 H: 7.34 N: 4.08. Found (%) C: 69.95 H: 7.52 N: 4.34.

EXAMPLE 49

3-Cyclohexyl-5-(N,N-diethylaminomethyl)-4-hydroxyphenyl 2-thienyl ketone hydrochloride.

M.p. 204°–206° C. (ethanol).
Elem. Anal. ($C_{22}H_{29}NO_2S.HCl$): Calcd (%) C: 64.77 H: 7.41 N: 3.43. Found (%) C: 64.67 H: 7.51 N: 3.68.

EXAMPLE 50

3-Cyclohexyl-5-(N,N-dimethylaminomethyl)-4-hydroxybenzophenone hydrochloride.

M.p. 223°–225° C. (ethanol).
Elem. Anal. ($C_{22}H_{27}NO_2S.HCl$): Calcd (%) C: 70.67 H: 7.55 N: 3.75. Found (%) C: 70.56 H: 7.49 N: 3.81.

EXAMPLE 51

3-(N,N-Dimethylaminomethyl)-4-hydroxy-5-(1-methylpropyl)benzophenone hydrochloride.

M.p. 135°–136° C. (ethanol).
Elem. Anal. ($C_{20}H_{25}NO_2.HCl$): Calcd (%) C: 69.05 H: 7.53 N: 4.03. Found (%) C: 68.98 H: 7.70 N: 4.15.

EXAMPLE 52

3-(N,N-Dimethylaminomethyl)-4-hydroxy-5-(1-methylpropyl)phenyl 2-thienyl ketone hydrochloride.

M.p. 168°–169° C. (isopropanol).
Elem. Anal. ($C_{18}H_{23}NO_2S.HCl$): Calcd (%) C: 61.09 H: 6.84 N: 3.96. Found (%) C: 61.06 H: 6.69 N: 4.08.

EXAMPLE 53

3-(1,1-Dimethylethyl)-4-hydroxy-5-(N-ethyl-N-methylaminomethyl)phenyl 2-thienyl ketone hydrochloride.

M.p. 202°–204° C. (ether/methanol).
Elem. Anal. ($C_{19}H_{25}NO_2S.HCl$): Calcd (%) C: 62.02 H: 7.12 N: 3.81. Found (%) C: 61.97 H: 7.02 N: 3.79.

EXAMPLE 54

3-(1,1-Dimethylethyl)-4-hydroxy-5-(N-methylaminomethyl)phenyl 2-thienyl ketone.

M.p. 128°–129° C. (ethanol/water).
Elem. Anal. ($C_{17}H_{21}NO_2S$): Calcd (%) C: 67.30 H: 6.98 N: 4.62. Found (%) C: 67.22 H: 7.00 N: 4.68.

EXAMPLE 55

3-(1,1-Dimethylethyl)-4-hydroxy-5-aminomethylphenyl 2-thienyl ketone hydrochloride.

M.p. 187°–188° C. (isopropanol/ether).
Elem. Anal. ($C_{16}H_{19}NO_2S.HCl$): Calcd (%) C: 58.98 H: 6.19 N: 4.30. Found (%) C: 59.06 H: 6.90 N: 4.30.

EXAMPLE 56

3-(1,1-Dimethylethyl)-4-hydroxy-5-[N-(2-hydroxyethyl)-N-methylaminomethyl]phenyl 2-thienyl ketone hydrochloride.

M.p. 176°–177.5° C. (ethanol).
Elem. Anal. ($C_{19}H_{25}NO_3S.HCl$): Calcd (%) C: 59.44 H: 6.83 N: 3.65. Found (%) C: 59.27 H: 6.78 N: 3.76.

EXAMPLE 57

3-(1,1-Dimethylethyl)-4-hydroxy-5-[N-methyl-N-propargyl)aminomethyl]phenyl 2-thienyl ketone.

M.p. 121°–123° C. (ethanol).
Elem. Anal. ($C_{20}H_{23}NO_2S$): Calcd (%) C: 70.35 H: 6.79 N: 4.10. Found (%) C: 70.31 H: 6.78 N: 4.06.

EXAMPLE 58

3-(1,1-Dimethylethyl)-4-hydroxy-5-[N-(2-hydroxyethyl)-N-ethylaminomethyl]phenyl 2-thienyl ketone hydrochloride.

M.p. 155°–156° C. (ethanol).
Elem. Anal. ($C_{20}H_{27}NO_3S.HCl$): Calcd (%) C: 60.36 H: 7.09 N: 3.52. Found (%) C: 60.18 H: 7.21 N: 3.47.

EXAMPLE 59

3-(1,1-Dimethylethyl)-4-hydroxy-5-(N,N-di-n-butylaminomethyl)phenyl 2-thienyl ketone hydrochloride.

M.p. 107°–108° C. (ethanol/ether).
Elem. Anal. ($C_{24}H_{35}NO_2S.HCl$): Calcd (%) C: 65.80 H: 8.28 N: 3.20. Found (%) C: 65.63 H: 8.48 N: 3.09.

EXAMPLE 60

3-(1,1-Dimethylethyl)-4-hydroxy-5-(N,N-diisopropylaminomethyl)phenyl 2-thienyl ketone hydrochloride.

M.p. 155°–156° C. (ethanol/ether).
Elem. Anal. ($C_{22}H_{31}NO_2S.HCl$): Calcd (%) C: 64.45 H: 7.87 N: 3.42. Found (%) C: 64.32 H: 7.90 N: 3.27.

EXAMPLE 61

3-(1,1-Dimethylethyl)-4-hydroxy-5-[N-(2-hydroxyethyl)-N-methylaminomethyl]phenyl 2-thienyl ketone benzenesulfonate.

M.p. 162°–163° C. (methanol/isopropyl ether).
Elem. Anal. ($C_{19}H_{25}NO_3S.C_6H_6O_3S$): Calcd (%) C: 59.38 H: 6.18 N: 2.77. Found (%) C: 59.32 H: 6.21 N: 3.04.

EXAMPLE 62

3-(1,1-Dimethylethyl)-4-hydroxy-5-[N-(2-acetyloxyethyl)-N-methylaminomethyl]phenyl 2-thienyl ketone.

M.p. 124°–126° C. (ethanol/water).
Elem. Anal. ($C_{21}H_{27}NO_4S$): Calcd (%) C: 64.76 H: 6.99 N: 3.60. Found (%) C: 64.72 H: 7.04 N: 3.67.

EXAMPLE 63

3-(1,1-Dimethylethyl)-4-hydroxy-5-[N-(2-hydroxyethyl)-N-methylaminomethyl]-4'-methylbenzophenone.

M.p. 131°–132° C. (ethanol/water).

Elem. Anal. ($C_{22}H_{29}NO_3$): Calcd (%) C: 74.33 H: 8.22 N: 3.94. Found (%) C: 74.25 H: 8.36 N: 4.17.

EXAMPLE 64

3-(1,1-Dimethylethyl)-4-hydroxy-5-[N-(2-hydroxyethyl)-N-methylaminomethyl]-4'-chlorobenzophenone.

M.p. 126°–127° C. (ethanol/water).

Elem. Anal. ($C_{21}H_{26}ClNO_3$): Calcd (%) C: 67.10 H: 6.97 N: 3.73. Found (%) C: 67.03 H: 6.97 N: 3.84.

EXAMPLE 65

3-(1,1-Dimethylethyl)-4-hydroxy-5-(N-n-butyl-N-ethylaminomethyl)phenyl 2-thienyl ketone hydrochloride.

M.p. 140°–142° C. (acetone/n-hexane).

Elem. Anal. ($C_{22}H_{31}NO_2S.HCl$): Calcd (%) C: 64.45 H: 7.87 N: 3.42. Found (%) C: 64.29 H: 8.00 N: 3.40.

EXAMPLE 66

3-(1,1-Dimethylethyl)-4-hydroxy-5-(N,N-dicyclohexylaminomethyl)phenyl 2-thienyl ketone.

M.p. 161°–162° C. (ethanol).

Elem. Anal. ($C_{28}H_{39}NO_2S$): Calcd (%) C: 74.13 H: 8.66 N: 3.09. Found (%) C: 74.00 H: 8.76 N: 2.96.

EXAMPLE 67

3-(1,1-Dimethylethyl)-4-hydroxy-5-[N-n-butyl-N-(2-hydroxyethyl)aminomethyl]phenyl 2-thienyl ketone hydrochloride.

M.p. 125°–128° C. (ethanol/ether).

Elem. Anal. ($C_{22}H_{31}NO_3S.HCl$): Calcd (%) C: 62.03 H: 7.57 N: 3.29. Found (%) C: 61.83 H: 7.57 N: 3.47.

EXAMPLE 68

3-(1,1-Dimethylethyl)-4-hydroxy-5-(N,N-di-n-hexylaminomethyl)phenyl 2-thienyl ketone hydrochloride.

M.p. 106°–108° C. (ethanol/ether).

Elem. Anal. ($C_{28}H_{43}NO_2S.HCl$): Calcd (%) C: 68.05 H: 8.97 N: 2.83. Found (%) C: 67.70 H: 8.99 N: 2.94.

EXAMPLE 69

3-(1,1-Dimethylethyl)-4-hydroxy-5-(N-allyl-N-cyclohexylaminomethyl)phenyl 2-thienyl ketone hydrochloride.

M.p. 154°–156° C. (ethanol/ether).

Elem. Anal. ($C_{25}H_{33}NO_2S.HCl$): Calcd (%) C: 67.02 H: 7.65 N: 3.13. Found (%) C: 66.95 H: 7.62 N: 3.07.

EXAMPLE 70

3-(1,1-Dimethylethyl)-4-hydroxy-5-(N,N-di-n-octylaminomethyl)phenyl 2-thienyl ketone hydrochloride.

M.p. 90°–91° C. (ether/n-hexane).

Elem. Anal. ($C_{32}H_{51}NO_2S.HCl$): Calcd (%) C: 69.85 H: 9.52 N: 2.55. Found (%) C: 69.75 H: 9.39 N: 2.51.

EXAMPLE 71

3-(1,1-Dimethylethyl)-4-hydroxy-5-[N-cyclohexyl-N-(2-hydroxyethyl)aminomethyl]phenyl 2-thienyl ketone hydrochloride.

M.p. 156°–157° C. (isopropanol).

Elem. Anal. ($C_{24}H_{33}NO_3S.HCl$): Calcd (%) C: 63.77 H: 7.58 N: 3.10. Found (%) C: 63.50 H: 7.55 N: 3.03.

EXAMPLE 72

3-(1,1-Dimethylethyl)-4-hydroxy-5-[N-(2-hydroxyethyl)-N-methylaminomethyl]-2'-fluorobenzophenone.

M.p. 87°–89° C. (ethanol/water).

Elem. Anal. ($C_{21}H_{26}FNO_3$): Calcd (%) C: 70.17 H: 7.29 N: 3.90. Found (%) C: 69.99 H: 7.27 N: 4.04.

EXAMPLE 73

3-(1,1-Dimethylethyl)-4-hydroxy-5-[N-(2-hydroxyethyl)-N-methylaminomethyl]benzophenone.

M.p. 118°–119° C. (ethanol/water).

Elem. Anal. ($C_{21}H_{27}NO_3$): Calcd (%) C: 73.87 H: 7.97 N: 4.10. Found (%) C: 73.80 H: 8.06 N: 3.98.

EXAMPLE 74

3-(1-Methylpropyl)-4-hydroxy-5-[N-(2-hydroxyethyl)-N-methylaminomethyl]benzophenone hydrochloride.

M.p. 67°–70° C. (ethanol/isopropyl ether).

Elem. Anal. ($C_{21}H_{27}NO_3.HCl.H_2O$): Calcd (%) C: 63.71 H: 7.64 N: 3.54. Found (%) C: 63.31 H: 7.61 N: 3.51.

EXAMPLE 75

3-(1,1-Dimethylethyl)-4-hydroxy-5-[N-(2-hydroxyethyl)-N-methylaminomethyl]phenyl 2-thienyl ketone phosphate.

M.p. 137°–140° C. (ethyl acetate).

Elem. Anal. ($C_{19}H_{25}NO_3S.H_3O_4P$): Calcd (%) C: 51.23 H: 6.34 N: 3.14. Found (%) C: 51.09 H: 6.44 N: 2.68.

EXAMPLE 76

3-Cyclohexyl-4-hydroxy-5-[N-(2-hydroxyethyl)-N-methylaminomethyl]benzophenone.

M.p. 92°–93° C. (isopropyl ether/n-hexane).

Elem. Anal. ($C_{23}H_{29}NO_3$): Calcd (%) C: 75.17 H: 7.95 N: 3.81. Found (%) C: 75.18 H: 8.24 N: 3.67.

EXAMPLE 77

3-(1-Methylethyl)-4-hydroxy-5-[N-methyl-N-(2-hydroxyethyl)aminomethyl]phenyl 2-thienyl ketone hydrochloride.

M.p. 125°–128° C. (isopropanol/ether).

Elem. Anal. ($C_{18}H_{23}NO_3S.HCl.\frac{1}{2}H_2O$): Calcd (%) C: 57.74 H: 6.60 N: 3.74. Found (%) C: 57.76 H: 6.71 N: 3.81.

EXAMPLE 78

3-(1-Methylpropyl)-4-hydroxy-5-[N-methyl-N-(2-hydroxyethyl)aminomethyl]phenyl 2-thienyl ketone hydrochloride.

M.p. 114°–117° C. (isopropanol/ethyl acetate).

Elem. Anal. ($C_{19}H_{25}NO_3S.HCl$): Calcd (%) C: 59.44 H: 6.83 N: 3.65. Found (%) C: 59.30 H: 7.13 N: 3.73.

EXAMPLE 79

3-(1,1-Dimethylethyl)-4-hydroxy-5-[N-n-butyl-N-(carbamoylmethyl)aminomethyl]phenyl 2-thienyl ketone.

M.p. 146°-147° C. (ether).

Elem. Anal. ($C_{22}H_{30}N_2O_3S \cdot \frac{1}{2}H_2O$): Calcd (%) C: 64.68 H: 7.68 N: 6.86. Found (%) C: 64.59 H: 7.52 N: 6.75.

EXAMPLE 80

3-(1,1-Dimethylethyl)-4-hydroxy-5-[N-(2-hydroxyethyl)-N-methylaminomethyl]-2'-trifluoromethylbenzophenone hydrochloride.

M.p. 175°-176° C. (ethyl acetate/ether).

Elem. Anal. ($C_{22}H_{26}F_3NO_3S \cdot HCl$): Calcd (%) C: 59.26 H: 6.10 N: 3.14. Found (%) C: 59.37 H: 6.29 N: 3.13.

EXAMPLE 81

3-(1,1-Dimethylethyl)-4-hydroxy-5-[N-(2-hydroxyethyl)-N-methylaminomethyl]-2',6'-dichlorobenzophenone hydrochloride.

M.p. 122°-124° C. (ethyl acetate).

Elem. Anal. ($C_{21}H_{25}Cl_2NO_3S \cdot HCl$): Calcd (%) C: 56.46 H: 5.87 N: 3.13. Found (%) C: 56.16 H: 6.06 N: 3.10.

EXAMPLE 82

3-(1,1-Dimethylethyl)-4-hydroxy-5-[N-(2-hydroxyethyl)aminomethyl]phenyl 2-thienyl ketone.

M.p. 145°-146° C. (ethyl acetate).

Elem. Anal. ($C_{18}H_{23}NO_3S$): Calcd (%) C: 64.84 H: 6.95 N: 4.20. Found (%) C: 64.81 H: 7.14 N: 3.81.

EXAMPLE 83

5-(N-Carboxymethyl-N-methylaminomethyl)-3-(1,1-dimethylethyl)-4-hydroxyphenyl 2-thienyl ketone.

M.p. 180°-182° C. (ethanol/water).

Elem. Anal. ($C_{19}H_{23}NO_4S$): Calcd (%) C: 63.14 H: 6.41 N: 3.88. Found (%) C: 62.86 H: 6.57 N: 3.73.

EXAMPLE 84

3-(1,1-Dimethylethyl)-4-hydroxy-5-[N-(3-hydroxypropyl)-N-methylaminomethyl]phenyl 2-thienyl ketone hydrochloride.

M.p. 146°-148° C. (ethanol/isopropyl ether).

Elem. Anal. ($C_{20}H_{27}NO_3S \cdot HCl$): Calcd (%) C: 60.36 H: 7.09 N: 3.52. Found (%) C: 60.19 H: 7.17 N: 3.68.

Compounds of the present invention exhibit superior analgesic, anti-inflammatory and anti-pyretic activity as compared to prior art compounds, including R-830. Furthermore, the toxicity of compounds of the present invention is lower than R-830.

Test data showing the activity and superiority for compounds representative of those of the present invention is set forth below. In the tests, a representative compound of the present invention, namely 3-(1,1-Dimethylethyl)-4-hydroxy-5-[N-(2-hydroxyethyl)-N-methylaminomethyl]phenyl-2-thienyl ketone, the compound described in Example 4 (the "test compound"), was dissolved or suspended in 0.5% methylcellulose (MC) and administered as described.

(1) Inhibitory Action to Carrageenin Edema

Seven male rats (SD strain; 6 weeks of age) were used in a group. The test compound was administered per os and, after one hour, 0.1 ml of 0.5% λ-carrageenin solution was injected subcutaneously into the right hind paw. After three hours, the volume of the right hind paw was measured with a plethysmometer (UGO-BASILE). The degree of swelling was calculated by subtracting the volume before the carrageenin from the post injection volume. Based on the degree of swelling exhibited by the drug-treated group compared to that of a control group, an inhibitory rate was obtained and an $ED_{30}$ value was calculated.

(2) Inhibitory Action to Acetic Acid Writhing

Six male mice (ddY strain; five weeks of age) were used in a group. The test compound was administered per os and, after one hour, 0.6% acetic acid was intraperitoneally injected at the dose of 0.1 ml/10 g and the total writhings within 20 minutes thereafter were counted. By comparing the number of writhings of the drug-treated group to that of the control group, the inhibitory rate was obtained and an $ED_{50}$ value was calculated.

(3) Inhibitory Action to Pain by Heat Stimulation

Ten male mice (ddY strain; five weeks of age) were used in a group. Radiated heat (250 watts; 4 cm distance from the heat source) was applied to the end of the tail of the mice. Mice which showed a tail flick within 4 to 7 seconds were selected and subjected to the experiment. The test compound was administered per os and the time of appearance of the tail flick after 5, 15, 30, 45 and 60 minutes was measured. The mice which showed a tail flick at greater than the sum of 30 plus the average time needed for showing tail flick before administration of the drug were judged to be analgesically positive. The maximum positive rate among the analgesically positive rates in each measuring time was defined as the analgesically positive rate at that dose and an $ED_{50}$ value was calculated therefrom.

(4) Stomach Disorder

Ten male rats (SD strain; five weeks of age) were used in a group. The test compound dissolved or suspended in physiological saline solution was administered to them per os. The animals were than fasted for 17 hours, and 0.5 ml of 5% pontamine sky blue solution was injected intravenously and, after 10 minutes, they were sacrificed with ether. The stomach was removed from the animals, and about 8 ml of 5% formaline solution was injected into the stomach to provide a semifixing. The presence of the edema was checked using a stereoscopic microscope. Rats in which even one ulcer was observed was judged to be positive in ulcer generation and a $UD_{50}$ value was calculated by a provit method.

(5) Acute Toxicity

Four male rats (SD strain; six weeks of age) were used in a group. The test compound was given per os and, after 7 days, the mice were monitored for life and an $LD_{50}$ value was calculated by a provit method.

TABLE 1

| Tests | Cmpd of Example 4 | R-830 | Indomethacin | Thiaramide |
|---|---|---|---|---|
| (1) $ED_{30}$ (mg/kg) | 9.8 | 5.6 | 0.8 | 112.2 |
| (2) $ED_{50}$ (mg/kg) | 16.4 | 22.4 | 2.1 | 27.3 |
| (3) $ED_{50}$ (mg/kg) | 47.0 | *(1) | *(2) | 108.5 |
| (4) $UD_{50}$ (mg/kg) | 146.4 | 11.8 | 2.4 | 277.6 |
| (5) $LD_{50}$ (mg/kg) | 1000 | 1625* | 29* | 4700* |
| Safety Region | 14.9 | 2.1 | 3.0 | 2.5 |

TABLE 1-continued

|  | Cmpd of Example 4 | R-830 | Indomethacin | Thiaramide |
|---|---|---|---|---|
| ($UD_{50}/ED_{50}$) |  |  |  |  |

*values given in literature
*(1): no action at 500 mg/kg
*(2): no action at 20 mg/kg It is apparent from the data in Table 1 that the test compound exhibits two characteristic features of basic and acidic anti-inflammatory agents and shows strong analgesic and anti-inflammatory activity.

The test compound exhibited analgesic activity as strong as codeine not only to inflammatory pain (such as acetic acid writhing) but also to non-inflammatory pain such as heat stimulation. At the same time, the test compound exhibited inhibitory action to carrageenin edema.

The compounds of the present invention thus show excellent analgesic and anti-inflammatory actions which are not achieved in the conventional drugs. Moreover, their ulcer generation action and toxicity are very low. Accordingly, their safety region is quite broad and, therefore, they can be used as a safe remedy for various pains, arthritis, rheumatism, and upper airway inflammation of mammalia including humans.

What is claimed is:

1. A compound of the formula

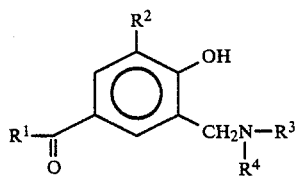

or a pharmaceutically acceptable salt thereof, wherein:
$R^1$ is

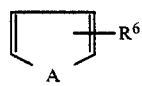

wherein A is sulfur, and $R^6$ is hydrogen, straight or branched chain alkyl of 1 to 4 carbon atoms or halo;
$R^2$ is straight or branched chain alkyl of 1 to 4 carbon atoms or cycloalkyl of 5 to 7 carbon atoms; and
$R^3$ and $R^4$ are the same or different and each is hydrogen; straight or branched chain alkyl of 1 to 8 carbon atoms unsubstituted or substituted by hydroxy, acyloxy of 2 to 5 carbon atoms, carboxyl or carbamoyl; straight or branched chain alkenyl of 2 to 6 carbon atoms; straight or branched chain alkynyl of 2 to 6 carbon atoms; or cycloalkyl of 5 to 7 carbon atoms.

2. A compound according to claim 1, wherein $R^2$ is straight or branched chain alkyl of 1 to 4 carbon atoms.

3. A compound according to claim 1, wherein $R^2$ is cycloalkyl of 5 to 7 carbon atoms.

4. A compound according to claim 1, wherein $R^3$ and $R^4$ are hydrogen.

5. A compound according to claim 1, wherein $R^1$ is 2-thienyl or 3-thienyl.

6. A compound according to claim 1, wherein $R^3$ and $R^4$ are the same or different and each is hydrogen or straight or branched chain alkyl of 1 to 4 carbon atoms.

7. A compound according to claim 1 in the form of a pharmaceutically acceptable salt.

8. A compound according to claim 1 which is 3-(1,1-Dimethylethyl)-4-hydroxy-5-[N-(2-hydroxyethyl)-N-methylaminomethyl]phenyl 2-thienyl ketone;
3-(N,N-Dimethylaminomethyl)-5-(1,1-dimethylethyl)-4-hydroxyphenyl 2-thienyl ketone;
3-(N,N-Dimethylaminomethyl)-5-(1,1-dimethylethyl)-4-hydroxyphenyl 2-thienyl ketone hydrochloride;
3-(N,N-Diethylaminomethyl)-5-(1,1-dimethylethyl)-4-hydroxyphenyl 2-thienyl ketone hydrochloride;
3-(N,N-Dimethylaminomethyl)-5-(1,1-dimethylethyl)-4-hydroxyphenyl 5-methyl-2-thienyl ketone;
3-(N,N-Dimethylaminomethyl)-5-(1,1-dimethylethyl-4-hydroxyphenyl 5-chloro-2-thienyl ketone;
3-(N,N-Dimethylaminomethyl)-5-(1,1-dimethylethyl)-4hydroxyphenyl 5-bromo-2-thienyl ketone;
3-(1,1-Dimethylethyl)-4-hydroxy-5-bis(2-hydroxyethyl)aminomethylphenyl 2-thienyl ketone;
3-(N,N-Dimethylaminomethyl)-5-(1,1-dimethylethyl)-4-hydroxyphenyl 3-chloro-2-thienyl ketone;
3-(N,N-Dimethylaminomethyl)-5-(1,1-dimethylethyl)-4-hydroxyphenyl 3-methyl-2-thienyl ketone;
3-(N,N-Dimethylaminomethyl-5-(1,1-dimethylethyl)-4-hydroxyphenyl 4-methyl-2-thienyl ketone hydrochloride;
3-(N,N-Dimethylaminomethyl)-4-hydroxy-5-(1-methylethyl)phenyl 2-thienyl ketone hydrochloride;
3-(N,N-Diethylaminomethyl)-4-hydroxy-5-(1-methylethyl)phenyl 2-thienyl ketone hydrochloride;
3-Cyclohexyl-5-(N,N-dimethylaminomethyl)-4-hydroxyphenyl 2-thienyl ketone;
3-Cyclohexyl-5-(N,N-diethylaminomethyl)-4-hydroxyphenyl 2-thienyl ketone hydrochloride;
3-(N,N-Dimethylaminomethyl)-4-hydroxy-5-(1-methylpropyl)phenyl 2-thienyl ketone hydrochloride;
3-(1,1-Dimethylethyl)-4-hydroxy-5-(N-ethyl-N-methylaminomethyl)phenyl 2-thienyl ketone hydrochloride;
3-(1,1-Dimethylethyl)-4-hydroxy-5-(N-methylaminomethyl)phenyl 2-thienyl ketone;
3-(1,1-Dimethylethyl)-4-hydroxy-5-aminomethylphenyl 2-thienyl ketone hydrochloride;
3-(1,1-Dimethylethyl)-4-hydroxy-5-[N-(2-hydroxyethyl)-N-methylaminomethyl]phenyl 2-thienyl ketone hydrochloride;
3-(1,1-Dimethylethyl)-4-hydroxy-5-[N-methyl-N-propargyl)aminomethyl]phenyl 2-thienyl ketone;
3-(1,1-Dimethylethyl)-4-hydroxy-5-[N-(2-hydroxyethyl)-N-ethylaminomethyl]phenyl 2-thienyl ketone hydrochloride;
3-(1,1-Dimethylethyl)-4-hydroxy-5-(N,N-di-n-butylaminomethyl)phenyl 2-thienyl ketone hydrochloride;
3-(1,1-Dimethylethyl)-4-hydroxy-5-(N,N-di-isopropylaminomethyl)phenyl 2-thienyl ketone hydrochloride;
3-(1,1-Dimethylethyl)-4-hydroxy-5-[N-(2-hydroxyethyl)-N-methylaminomethyl]phenyl 2-thienyl ketone benzenesulfonate;
3-(1,1-Dimethylethyl)-4-hydroxy-5-[N-(2-acetyloxyethyl)-N-methylaminomethyl]phenyl 2-thienyl ketone;

3-(1,1-Dimethylethyl)-4-hydroxy-5-(N-n-butyl-N-ethylaminomethyl)phenyl 2-thienyl ketone hydrochloride;
3-(1,1-Dimethylethyl)-4-hydroxy-5-(N,N-di-cyclohexylaminomethyl)phenyl 2-thienyl ketone;
3-(1,1-Dimethylethyl)-4-hydroxy-5-[N-n-butyl-N-(2-hydroxyethyl)aminomethyl]phenyl 2-thienyl ketone hydrochloride;
3-(1,1-Dimethylethyl)-4-hydroxy-5-(N,N-di-n-hexylaminomethyl)phenyl 2-thienyl ketone hydrochloride;
3-(1,1-Dimethylethyl)-4-hydroxy-5-(N-allyl-N-cyclohexylaminomethyl)phenyl 2-thienyl ketone hydrochloride;
3-(1,1-Dimethylethyl)-4-hydroxy-5-(N,N-di-n-octylaminomethyl)phenyl 2-thienyl ketone hydrochloride;
3-(1,1-Dimethylethyl)-4-hydroxy-5-[N-cyclohexyl-N-(2-hydroxyethylaminomethyl]phenyl 2-thienyl ketone hydrochloride;
3-(1,1-Dimethylethyl)-4-hydroxy-5-[N-(2-hydroxyethyl)-N-methylaminomethyl]phenyl 2-thienyl ketone phosphate;
3-(1-Methylethyl)-4-hydroxy-5-[N-methyl-N-(2-hydroxyethyl)aminomethyl]phenyl 2-thienyl ketone hydrochloride;
3-(1-Methylpropyl)-4-hydroxy-5-[N-methyl-N-(2-hydroxyethyl)aminomethyl]phenyl 2-thienyl ketone hydrochloride;
3-(1,1-Dimethylethyl)-4-hydroxy-5-[N-n-butyl-N-(carbamoylmethyl)aminomethyl]phenyl 2-thienyl ketone;
3-(1,1-Dimethylethyl)-4-hydroxy-5-[N-(2-hydroxyethyl)aminomethyl]phenyl 2-thienyl ketone;
5-(N-Carboxymethyl-N-methylaminomethyl)-3-(1,1-dimethylethyl)-4-hydroxyphenyl 2-thienyl ketone; or
3-(1,1-Dimethylethyl)-4-hydroxy-5-[N-(3-hydroxypropyl)-N-methylaminomethyl]phenyl 2-thienyl ketone hydrochloride.

9. A pharmaceutical composition useful for effecting analgesic, anti-inflammatory, and anti-pyretic action in humans and animals which comprises a therapeutically effective amount of a compound of the formula

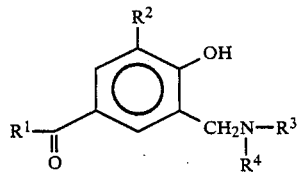

or a pharmaceutically acceptable salt thereof, wherein:
$R^1$ is

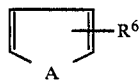

wherein A is sulfur, and $R^6$ is hydrogen, straight or branched chain alkyl of 1 to 4 carbon atoms or halo;
$R^2$ is straight or branched chain alkyl of 1 to 4 carbon atoms or cycloalkyl of 5 to 7 carbon atoms; and
$R^3$ and $R^4$ are the same or different and each is hydrogen; straight or branched chain alkyl of 1 to 8 carbon atoms unsubstituted or substituted by hydroxy, acyloxy of 2 to 5 carbon atoms, carboxyl or carbamoyl; straight or branched chain alkenyl of 2 to 6 carbon atoms; straight or branched chain alkynyl of 2 to 6 carbon atoms; or cycloalkyl of 5 to 7 carbon atoms, in combination with a pharmaceutically acceptable carrier.

10. A pharmaceutical composition according to claim 9, wherein $R^1$ is 2-thienyl or 3-thienyl.
11. A pharmaceutical composition according to claim 9, wherein $R^2$ is straight or branched chain alkyl of 1 to 4 carbon atoms.
12. A pharmaceutical composition according to claim 9, wherein $R^2$ is cycloalkyl of 5 to 7 carbon atoms.
13. A pharmaceutical composition according to claim 9, wherein $R^3$ and $R^4$ are hydrogen.
14. A pharmaceutical composition according to claim 9, wherein $R^3$ and $R^4$ are the same or different and each is hydrogen or straight or branched chain alkyl of 1 to 4 carbon atoms.
15. A pharmaceutical composition according to claim 9, wherein the compound is in the form of a pharmaceutically acceptable salt.
16. A pharmaceutical composition according to claim 9 where in the compound is 3-(1,1-Dimethylethyl)-4-hydroxy-5-[N-(2-hydroxyethyl)-N-methylaminomethyl]phenyl 2-thienyl ketone;
3-(N,N-Dimethylaminomethyl)-5-(1,1-dimethylethyl)-4-hydroxyphenyl 2-thienyl ketone;
3-(N,N-Dimethylaminomethyl)-5-(1,1-dimethylethyl)-4-hydroxyphenyl 2-thienyl ketone hydrochloride;
3-(N,N-Diethylaminomethyl)-5-(1,1-dimethylethyl)-4-hydroxyphenyl 2-thienyl ketone hydrochloride;
3-(N,N-Dimethylaminomethyl)-5-(1,1-dimethylethyl)-4-hydroxyphenyl 5-methyl-2-thienyl ketone;
3-(N,N-Dimethylaminomethyl)-5-(1,1-dimethylethyl-4-hydroxyphenyl 5-chloro-2-thienyl ketone;
3-(N,N-Dimethylaminomethyl)-5-(1,1-dimethylethyl)-4hydroxyphenyl 5-bromo-2-thienyl ketone;
3-(1,1-Dimethylethyl)-4-hydroxy-5-bis(2-hydroxyethyl) aminomethylphenyl 2-thienyl ketone;
3-(N,N-Dimethylaminomethyl)-5-(1,1-dimethylethyl)-4-hydroxyphenyl 3-chloro-2-thienyl ketone;
3-(N,N-Dimethylaminomethyl)-5-(1,1-dimethylethyl)-4-hydroxyphenyl 3-methyl-2-thienyl ketone;
3-(N,N-Dimethylaminomethyl-5-(1,1-dimethylethyl)-4-hydroxyphenyl 4-methyl-2-thienyl ketone hydrochloride;
3-(N,N-Dimethylaminomethyl)-4-hydroxy-5-(1-methylethyl)phenyl 2-thienyl ketone hydrochloride;
3-(N,N-Diethylaminomethyl)-4-hydroxy-5-(1-methylethyl)phenyl 2-thienyl ketone hydrochloride;
3-Cyclohexyl-5-(N,N-dimethylaminomethyl)-4-hydroxyphenyl 2-thienyl ketone;
3-Cyclohexyl-5-(N,N-diethylaminomethyl)-4-hydroxyphenyl 2-thienyl ketone hydrochloride;
3-(N,N-Dimethylaminomethyl)-4-hydroxy-5-(1-methylpropyl)phenyl 2-thienyl ketone hydrochloride;
3-(1,1-Dimethylethyl)-4-hydroxy-5-(N-ethyl-N-methylaminomethyl)phenyl 2-thienyl ketone hydrochloride;
3-(1,1-Dimethylethyl)-4-hydroxy-5-(N-methylaminomethyl)phenyl 2-thienyl ketone;
3-(1,1-Dimethylethyl)-4-hydroxy-5-aminomethylphenyl 2-thienyl ketone hydrochloride;
3-(1,1-Dimethylethyl)-4-hydroxy-5-[N-(2-hydroxyethyl)-N-methylaminomethyl]phenyl 2-thienyl ketone hydrochloride; 3-(1,1-Dimethylethyl)-4-hydroxy-5-

[N-methyl-N-propargyl)aminomethyl]phenyl 2-thienyl ketone;

3-(1,1-Dimethylethyl)-4-hydroxy-5-[N-(2-hydroxyethyl)-N-ethylaminomethyl]phenyl 2-thienyl ketone hydrochloride;

3-(1,1-Dimethylethyl)-4-hydroxy-5-(N,N-di-n-butylaminomethyl)phenyl 2-thienyl ketone hydrochloride;

3-(1,1-Dimethylethyl)-4-hydroxy-5-(N,N-di-isopropylaminomethyl)phenyl 2-thienyl ketone hydrochloride;

3-(1,1-Dimethylethyl)-4-hydroxy-5-[N-(2-hydroxyethyl)-N-methylaminomethyl]phenyl 2-thienyl ketone benzenesulfonate;

3-(1,1-Dimethylethyl)-4-hydroxy-5-[N-(2-acetyloxyethyl)-N-methylaminomethyl]phenyl 2-thienyl ketone;

3-(1,1-Dimethylethyl)-4-hydroxy-5-(N-n-butyl-N-ethylaminomethyl)phenyl 2-thienyl ketone hydrochloride;

3-(1,1-Dimethylethyl)-4-hydroxy-5-(N,N-di-cyclohexylaminomethyl)phenyl 2-thienyl ketone;

3-(1,1-Dimethylethyl)-4-hydroxy-5-[N-n-butyl-N-(2-hydroxyethyl)aminomethyl]phenyl 2-thienyl ketone hydrochloride;

3-(1,1-Dimethylethyl)-4-hydroxy-5-(N,N-di-n-hexylaminomethyl)phenyl 2-thienyl ketone hydrochloride;

3-(1,1-Dimethylethyl)-4-hydroxy-5-(N-allyl-N-cyclohexylaminomethyl)phenyl 2-thienyl ketone hydrochloride;

3-(1,1-Dimethylethyl)-4-hydroxy-5-(N,N-di-n-octylaminomethyl)phenyl 2-thienyl ketone hydrochloride;

3-(1,1-Dimethylethyl)-4-hydroxy-5-[N-cyclohexyl-N-(2-hydroxyethylaminomethyl]phenyl 2-thienyl ketone hydrochloride;

3-(1,1-Dimethylethyl)-4-hydroxy-5-[N-(2-hydroxyethyl)-N-methylaminomethyl]phenyl 2-thienyl ketone phosphate;

3-(1-Methylethyl)-4-hydroxy-5-[N-methyl-N-(2-hydroxyethyl)aminomethyl]phenyl 2-thienyl ketone hydrochloride;

3-(1-Methylpropyl)-4-hydroxy-5-[N-methyl-N-(2-hydroxyethyl)aminomethyl]phenyl 2-thienyl ketone hydrochloride;

3-(1,1-Dimethylethyl)-4-hydroxy-5-[N-n-butyl-N-(carbamoylmethyl)aminomethyl]phenyl 2-thienyl ketone;

3-(1,1-Dimethylethyl)-4-hydroxy-5-[N-(2-hydroxyethyl)aminomethyl]phenyl 2-thienyl ketone;

5-(N-Carboxymethyl-N-methylaminomethyl)-3-(1,1-dimethylethyl)-4-hydroxyphenyl 2-thienyl ketone; or 3-(1,1-Dimethylethyl)-4-hydroxy-5-[N-(3-hydroxypropyl)-N-methylaminomethyl]phenyl 2-thienyl ketone hydrochloride.

17. A method of treating pain, inflammation and fever in humans and animals, which comprises administering to a human or animal in need thereof a therapeutically effective amount of a compound of the formula

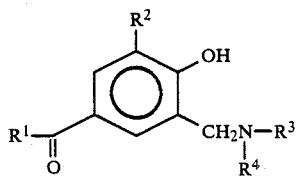

(I)

or a pharmaceutically acceptable salt thereof, wherein:
$R^1$ is

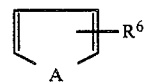

wherein A is sulfur, and $R^6$ is hydrogen, straight or branched chain alkyl of 1 to 4 carbon atoms or halo;

$R^2$ is straight or branched chain alkyl of 1 to 4 carbon atoms or cycloalkyl of 5 to 7 carbon atoms; and $R^3$ and $R^4$ are the same or different and each is hydrogen; straight or branched chain alkyl of 1 to 8 carbon atoms unsubstituted or substituted by hydroxy, acyloxy of 2 to 5 carbon atoms, carboxyl or carbamoyl; straight or branched chain alkenyl of 2 to 6 carbon atoms; straight or branched chain alkynyl of 2 to 6 carbon atoms; or cycloalkyl of 5 to 7 carbon atoms, in combination with a pharmaceutically acceptable carrier.

18. A method according to claim 17, wherein $R^1$ is 2-thienyl or 3-thienyl.

19. A method according to claim 17, wherein $R^2$ is straight or branched chain alkyl of 1 to 4 carbon atoms.

20. A method according to claim 17, wherein $R^2$ is cycloalkyl of 5 to 7 carbon atoms.

21. A method according to claim 17, wherein $R^3$ and $R^4$ are hydrogen.

22. A method according to claim 17, wherein $R^3$ and $R^4$ are the same or different, and each is hydrogen or straight or branched chain alkyl of 1 to 4 carbon atoms.

23. A method according to claim 17, wherein the compound is in the form of a pharmaceutically acceptable salt.

24. A compound according to claim 17 wherein the compound is 3-(1,1-Dimethylethyl)-4-hydroxy-5-[N-(2-hydroxyethyl)-N-methylaminomethyl]phenyl 2-thienyl ketone;

3-(N,N-Dimethylaminomethyl)-5-(1,1-dimethylethyl)-4-hydroxyphenyl 2-thienyl ketone;

3-(N,N-Dimethylaminomethyl)-5-(1,1-dimethylethyl)-4-hydroxyphenyl 2-thienyl ketone hydrochloride;

3-(N,N-Diethylaminomethyl)-5-(1,1-dimethylethyl)-4-hydroxyphenyl 2-thienyl ketone hydrochloride;

3-(N,N-Dimethylaminomethyl)-5-(1,1-dimethylethyl)-4-hydroxyphenyl 5-methyl-2-thienyl ketone;

3-(N,N-Dimethylaminomethyl)-5-(1,1-dimethylethyl-4-hydroxyphenyl 5-chloro-2-thienyl ketone;

3-(N,N-Dimethylaminomethyl)-5-(1,1-dimethylethyl)-4hydroxyphenyl 5-bromo-2-thienyl ketone;

3-(1,1-Dimethylethyl)-4-hydroxy-5-bis(2-hydroxyethyl)aminomethylphenyl 2-thienyl ketone;

3-(N,N-Dimethylaminomethyl)-5-(1,1-dimethylethyl)-4-hydroxyphenyl 3-chloro-2-thienyl ketone;

3-(N,N-Dimethylaminomethyl)-5-(1,1-dimethylethyl)-4-hydroxyphenyl 3-methyl-2-thienyl ketone;

3-(N,N-Dimethylaminomethyl-5-(1,1-dimethylethyl)-4-hydroxyphenyl 4-methyl-2-thienyl ketone hydrochloride;

3-(N,N-Dimethylaminomethyl)-4-hydroxy-5-(1-methylethyl)phenyl 2-thienyl ketone hydrochloride;

3-(N,N-Diethylaminomethyl)-4-hydroxy-5-(1-methylethyl)phenyl 2-thienyl ketone hydrochloride;

3-Cyclohexyl-5-(N,N-dimethylaminomethyl)-4-hydroxyphenyl 2-thienyl ketone;

3-Cyclohexyl-5-(N,N-diethylaminomethyl)-4-hydroxyphenyl 2-thienyl ketone hydrochloride;

3-(N,N-Dimethylaminomethyl)-4-hydroxy-5-(1-methylpropyl)phenyl 2-thienyl ketone hydrochloride;

3-(1,1-Dimethylethyl)-4-hydroxy-5-(N-ethyl-N-methylaminomethyl)phenyl 2-thienyl ketone hydrochloride;

3-(1,1-Dimethylethyl)-4-hydroxy-5-(N-methylaminomethyl)phenyl 2-thienyl ketone;

3-(1,1-Dimethylethyl)-4-hydroxy-5-aminomethylphenyl 2-thienyl ketone hydrochloride;

3-(1,1-Dimethylethyl)-4-hydroxy-5-[N-(2-hydroxyethyl)-N-methylaminomethyl]phenyl 2-thienyl ketone hydrochloride;

3-(1,1-Dimethylethyl)-4-hydroxy-5-[N-methyl-N-propargyl)aminomethyl]phenyl 2-thienyl ketone;

3-(1,1-Dimethylethyl)-4-hydroxy-5-[N-(2-hydroxyethyl)-N-ethylaminomethyl]phenyl 2-thienyl ketone hydrochloride;

3-(1,1-Dimethylethyl)-4-hydroxy-5-(N,N-di-n-butylaminomethyl)phenyl 2-thienyl ketone hydrochloride;

3-(1,1-Dimethylethyl)-4-hydroxy-5-(N,N-di-isopropylaminomethyl)phenyl 2-thienyl ketone hydrochloride;

3-(1,1-Dimethylethyl)-4-hydroxy-5-[N-(2-hydroxyethyl)-N-methylaminomethyl]phenyl 2-thienyl ketone benzenesulfonate;

3-(1,1-Dimethylethyl)-4-hydroxy-5-[N-(2-acetyloxyethyl)-N-methylaminomethyl]phenyl 2-thienyl ketone;

3-(1,1-Dimethylethyl)-4-hydroxy-5-(N-n-butyl-N-ethylaminomethyl)phenyl 2-thienyl ketone hydrochloride;

3-(1,1-Dimethylethyl)-4-hydroxy-5-(N,N-di-cyclohexylaminomethyl)phenyl 2-thienyl ketone;

3-(1,1-Dimethylethyl)-4-hydroxy-5-[N-n-butyl-N-(2-hydroxyethyl)aminomethyl]phenyl 2-thienyl ketone hydrochloride;

3-(1,1-Dimethylethyl)-4-hydroxy-5-(N,N-di-n-hexylaminomethyl)phenyl 2-thienyl ketone hydrochloride;

3-(1,1-Dimethylethyl)-4-hydroxy-5-(N-allyl-N-cyclohexylaminomethyl)phenyl 2-thienyl ketone hydrochloride;

3-(1,1-Dimethylethyl)-4-hydroxy-5-(N,N-di-n-octylaminomethyl)phenyl 2-thienyl ketone hydrochloride;

3-(1,1-Dimethylethyl)-4-hydroxy-5-[N-cyclohexyl-N-(2-hydroxyethylaminomethyl]phenyl 2-thienyl ketone hydrochloride;

3-(1,1-Dimethylethyl)-4-hydroxy-5-[N-(2-hydroxyethyl)-N-methylaminomethyl]phenyl 2-thienyl ketone phosphate;

3-(1-Methylethyl)-4-hydroxy-5-[N-methyl-N-(2-hydroxyethyl)aminomethyl]phenyl 2-thienyl ketone hydrochloride;

3-(1-Methylpropyl)-4-hydroxy-5-[N-methyl-N-(2-hydroxyethyl)aminomethyl]phenyl 2-thienyl ketone hydrochloride;

3-(1,1-Dimethylethyl)-4-hydroxy-5-[N-n-butyl-N-(carbamoylmethyl)aminomethyl]phenyl 2-thienyl ketone;

3-(1,1-Dimethylethyl)-4-hydroxy-5-[N-(2-hydroxyethyl)aminomethyl]phenyl 2-thienyl ketone;

5-(N-Carboxymethyl-N-methylaminomethyl)-3-(1,1-dimethylethyl)-4-hydroxyphenyl 2-thienyl ketone; or 3-(1,1-Dimethylethyl)-4-hydroxy-5-[N-(3-hydroxypropyl)-N-methylaminomethyl]phenyl 2-thienyl ketone hydrochloride.

* * * * *